US012714839B2

(12) United States Patent
Sen et al.

(10) Patent No.: US 12,714,839 B2
(45) Date of Patent: Aug. 25, 2026

(54) TECHNOLOGIES FOR NEEDLES WITH MICROCHANNELS

(71) Applicant: THE TRUSTEES OF INDIANA UNIVERSITY, Bloomington, IN (US)

(72) Inventors: Chandan K. Sen, Indianapolis, IN (US); Yi Xuan, Carmel, IN (US)

(73) Assignee: THE TRUSTEES OF INDIANA UNIVERSITY, Bloomington, IN (US)

(*) Notice: Subject to any disclaimer, the term of this patent is extended or adjusted under 35 U.S.C. 154(b) by 907 days.

(21) Appl. No.: 17/627,124

(22) PCT Filed: Jul. 17, 2020

(86) PCT No.: PCT/US2020/042510
§ 371 (c)(1),
(2) Date: Jan. 13, 2022

(87) PCT Pub. No.: WO2021/016074
PCT Pub. Date: Jan. 28, 2021

(65) Prior Publication Data

US 2022/0249821 A1 Aug. 11, 2022

Related U.S. Application Data

(60) Provisional application No. 62/903,298, filed on Sep. 20, 2019, provisional application No. 62/877,060, filed on Jul. 22, 2019.

(51) Int. Cl.
*A61M 37/00* (2006.01)
*A61N 1/32* (2006.01)

(52) U.S. Cl.
CPC ......... *A61M 37/0015* (2013.01); *A61N 1/327* (2013.01); *A61M 2037/0007* (2013.01);
(Continued)

(58) Field of Classification Search
CPC ...... A61M 37/0015; A61M 2037/0007; A61M 2037/0023; A61M 2037/003;
(Continued)

(56) References Cited

U.S. PATENT DOCUMENTS 6,312,612 B1 11/2001 Sherman
6,551,849 B1 4/2003 Kenney
(Continued)

FOREIGN PATENT DOCUMENTS

CN 103717249 4/2014
EP 1967581 A1 9/2008
(Continued)

OTHER PUBLICATIONS

Extended European Search Report for counterpart EP Application No. 20844275.6, dated Sep. 11, 2023.
(Continued)

*Primary Examiner* — Theodore J Stigell
*Assistant Examiner* — Benjamin Koo
(74) *Attorney, Agent, or Firm* — Barnes & Thornburg LLP

(57) ABSTRACT

An apparatus for delivering an agent to a target recipient includes a planar substrate having a first surface and a second surface, a reservoir defined in the first surface of the planar substrate, and a plurality of microstructures projecting from the second surface of the planar substrate. Each of the plurality of microstructures includes a delivery channel that extends from the reservoir to a channel opening defined in an exterior surface of the microstructure. In some embodiments, a needle with microchannels can be fabricated using a silicon wafer. A primary channel is etched into the wafer, and then a second silicon wafer can be bonded on top of the initial wafer. Microchannels can be formed from the primary channel to a surface of the wafer using deep reactive ion
(Continued)

etching. The diameter of the microchannels may be chosen for drug delivery. The illustrative diameter of the microchannels is 4 micrometers.

6 Claims, 14 Drawing Sheets

(52) U.S. Cl.
CPC ............... *A61M 2037/0023* (2013.01); *A61M 2037/003* (2013.01); *A61M 2037/0053* (2013.01); *A61M 2037/0061* (2013.01)

(58) Field of Classification Search
CPC .. A61M 2037/0038; A61M 2205/0244; A61M 5/3298; A61M 2037/0061; A61N 1/327
See application file for complete search history.

(56) References Cited

U.S. PATENT DOCUMENTS

| | | | | |
|---|---|---|---|---|
| 6,623,457 | B1 | 9/2003 | Rosenberg | |
| 11,235,132 | B2 | 2/2022 | Gallego-Perez et al. | |
| 2002/0133129 | A1 | 9/2002 | Arias et al. | |
| 2002/0193754 | A1 | 12/2002 | Cho | |
| 2002/0198512 | A1* | 12/2002 | Seward | A61M 37/0015 604/20 |
| 2003/0045837 | A1 | 3/2003 | Delmore | |
| 2004/0019331 | A1 | 1/2004 | Teshurun | |
| 2004/0164454 | A1 | 8/2004 | Gartstein | |
| 2004/0176732 | A1 | 9/2004 | Frazier | |
| 2005/0031676 | A1* | 2/2005 | Wong | A61B 10/0064 514/10.8 |
| 2006/0240543 | A1 | 10/2006 | Folch | |
| 2007/0275521 | A1 | 11/2007 | Fu | |
| 2010/0305516 | A1 | 12/2010 | Xu et al. | |
| 2011/0172609 | A1 | 7/2011 | Moga et al. | |
| 2012/0058506 | A1 | 3/2012 | Gao et al. | |
| 2012/0316503 | A1 | 12/2012 | Ross et al. | |
| 2013/0165861 | A1 | 6/2013 | Ross | |
| 2014/0148870 | A1 | 5/2014 | Burnett | |
| 2015/0051582 | A1 | 2/2015 | Pettis et al. | |
| 2015/0202418 | A1 | 7/2015 | Simon et al. | |
| 2016/0106965 | A1 | 4/2016 | Baker et al. | |
| 2016/0151616 | A1 | 6/2016 | Berry et al. | |
| 2017/0050010 | A1 | 2/2017 | Mcallister | |
| 2019/0117948 | A1 | 4/2019 | Berry et al. | |
| 2019/0216363 | A1 | 7/2019 | Holmes et al. | |
| 2019/0329014 | A1* | 10/2019 | Gallego-Perez | A61M 5/14 |
| 2019/0381256 | A1 | 12/2019 | Kodama | |
| 2020/0046957 | A1* | 2/2020 | Ogai | A61M 37/0015 |

FOREIGN PATENT DOCUMENTS

| | | | | |
|---|---|---|---|---|
| JP | 2011-013065 | A | 1/2011 | |
| JP | 2014-519344 | A | 8/2014 | |
| JP | 2014-519385 | A | 8/2014 | |
| JP | 2016-527001 | A | 9/2016 | |
| JP | 2018-171330 | A | 11/2018 | |
| WO | WO-0035530 | A1 * | 6/2000 | A61B 17/205 |
| WO | 2004076339 | | 9/2004 | |
| WO | 2008042404 | | 4/2008 | |
| WO | 2012/126784 | A1 | 9/2012 | |
| WO | 2012/168807 | A2 | 12/2012 | |
| WO | 2014/064534 | A2 | 5/2014 | |
| WO | 2018/181639 | A1 | 10/2018 | |

OTHER PUBLICATIONS

English translation of Office Action dated Aug. 29, 2024 and issued in counterpart Japanese Patent Appln. No. 2022-504143, 6 pages.
PCT International Search Report and Written Opinion completed by the ISA/US on Sep. 29, 2020 and issued in connection with PCT/US2020/042510.
Supp. Partial European Search Report for EP20844275, mailed Jul. 24, 2023.

* cited by examiner 100
110
122
120

112
114
D2
D1
124A
126
128A
130A
120A 124B
128B
130B
120B

D3
122

152
150
140
PHOTORESIST
154
D3

150
140
OXIDE
SI WAFER
142
144
D7

160
D4
D5
160
140
162
122

120A
130A
124
122
128A 158
156
140
144
122

124
D6
122
162

174
D8
174

172
170
140
144

174
176
176
174
128B
140

174
176
D9
176
140

174
174
120B 120B
124
124
D10
122
120B 174
174
140

120B
124
D11
124
122
120B

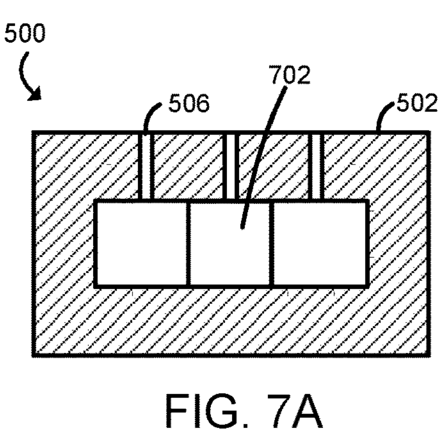
FIG. 7A
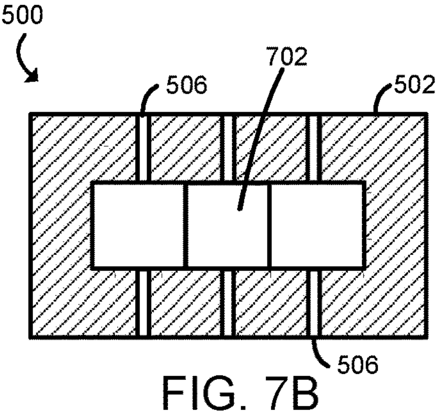
FIG. 7B
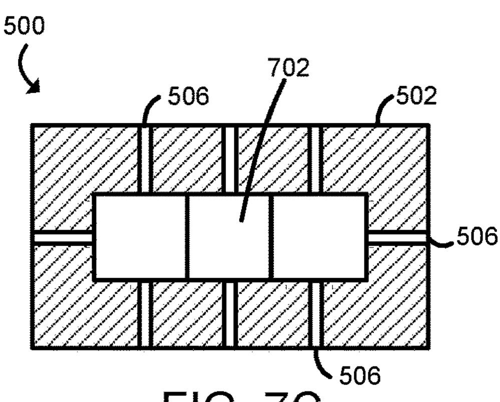
FIG. 7C
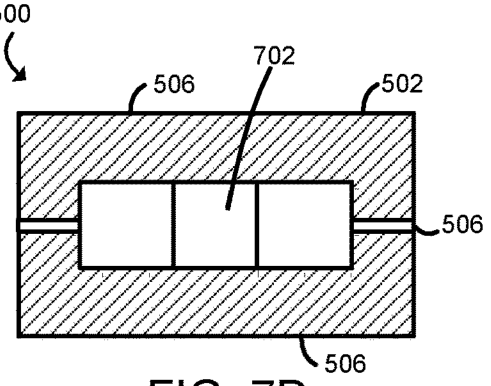
FIG. 7D
500
702 702 702
506 506 506 502
FIG. 7E
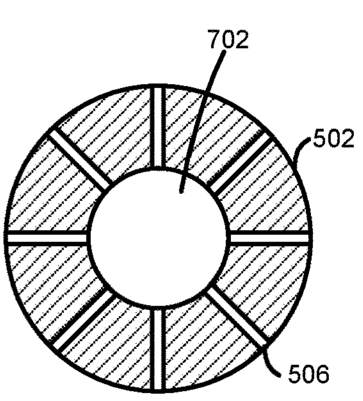
FIG. 7F
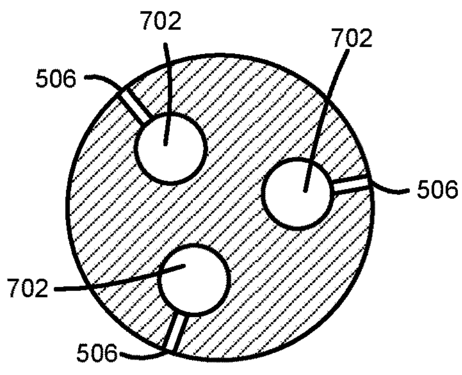
FIG. 7G

TECHNOLOGIES FOR NEEDLES WITH MICROCHANNELS

CROSS-REFERENCE TO RELATED APPLICATIONS

This application is a U.S. national counterpart application of international application serial No. PCT/US2020/042510 filed Jul. 17, 2020, which claims the benefit of provisional patent application No. 62/877,060, filed on Jul. 22, 2019, and entitled "MICRONEEDLE WITH NANOCHANNEL AND ASSOCIATED METHOD OF FABRICATION" and provisional patent application No. 62/903,298 filed on Sep. 20, 2019, and entitled "TECHNOLOGIES FOR NEEDLES WITH MICROCHANNELS," the disclosures of which are incorporated herein by reference.

TECHNICAL FIELD

The present disclosure relates generally to nanotechnology, and more particularly to nanochannels and nanochannel-based delivery methods.

BACKGROUND

A use of microneedle arrays has been proposed as a technique for delivering therapeutic agents across or into a biological tissue. The microneedles are adapted to disrupt the barrier function of the biological tissue and deliver therapeutic agents into a cell layer underneath a barrier (e.g., the outermost cell layer of a tissue). However, an aspect ratio of microneedles may significantly limit a capability of delivering the therapeutic agents to deeper cell layers of a tissue. For example, a longer microneedle may require a greater diameter for support to penetrate the biological barrier (e.g., the skin) to deliver the therapeutic agents to deeper cell layers, but the microneedles that have a diameter greater than a certain threshold may irreversibly disrupt the barrier function.

SUMMARY

The present application discloses one or more of the features recited in the appended claims and/or the following features which, alone or in any combination, may comprise patentable subject matter:

According to an aspect of the present disclosure, an apparatus for delivering an agent to a target recipient includes a planar substrate having a first surface and a second surface, a reservoir defined in the first surface of the planar substrate, and a plurality of microstructures projecting from the second surface of the planar substrate. Each of the plurality of microstructures includes a delivery channel that extends from the reservoir to a channel opening defined in an exterior surface of the microstructure. The reservoir is adapted to contain the agent to be delivered to the target recipient via the delivery channel. The delivery channel further includes a first channel having a first diameter and a second channel having a second diameter that is different than the first diameter.

According to another aspect of the present disclosure, a method for fabricating a microstructure array includes forming a substantially planar substrate having a first surface and a second surface, forming a plurality of microstructures projecting from at an angle from the second surface to a distal tip, forming a reservoir defined in the first surface, and forming a delivery channel in at least one of the microstructures that extends from the reservoir to a channel opening defined in an exterior of the corresponding microstructure. In various embodiments, the step of forming the microstructures may include semiconductor process, 3D printing, embossing, injection molding, casting, photochemical etching, electrochemical machining, electrical discharge machining, precision stamping, high-speed computer numerically controlled milling, Swiss screw machining, soft lithography, directional chemically assisted ion etching, or a combination thereof.

According to another aspect of the present disclosure, a method for delivering extracellular vesicles from one layer of cells to another layer of cells includes providing a microstructure array that has a planar substrate having a first surface and a second surface, a reservoir defined in the first surface of the planar substrate, and a plurality of microstructures projecting from the second surface of the planar substrate. Each of the plurality of microstructures includes a delivery channel that extends from the reservoir to a channel opening defined in an exterior surface of the microstructure. The reservoir is adapted to contain an agent to be delivered to the target recipient via the delivery channel.

According to another aspect of the present disclosure, a method for administering an agent to a subject using the apparatus disclosed above includes inserting the microstructures of the apparatus into the skin of the subject and causing the agent to be transported from the reservoir via the delivery channel of the microstructure and through the stratum corneum of the skin.

According to one aspect of the disclosure, an apparatus comprising a shaft extending from a proximal end to a distal end, the shaft defining a primary channel interior to the shaft extending from the proximal end toward the distal end, wherein the primary channel is open at the proximal end and closed at the distal end, wherein the shaft further defines one or more microchannels, wherein each of the one or more microchannels extends from the primary channel through a wall of the shaft, wherein each of the one or more microchannels has a diameter less than 1,000 micrometers.

In some embodiments, the one or more microchannels comprise a plurality of microchannels, wherein each of the plurality of microchannels extends from the primary channel through a side wall of the shaft.

In some embodiments, the shaft is silicon.

In some embodiments, the shaft is stainless steel.

In some embodiments, the shaft is plastic.

In some embodiments, each of the one or more microchannels has a diameter between 1 and 1,000 micrometers.

In some embodiments, the primary channel has a diameter between 10 and 1,000 micrometers.

In some embodiments, the primary channel has a length of at least one millimeters.

In some embodiments, the one or more microchannels comprises a plurality of microchannels, wherein each of the plurality of microchannels extends from the primary channel through a side wall of the shaft.

In some embodiments, the shaft comprises (i) a first wafer of silicon defining a bottom wall and two side walls of the primary channel and (ii) a second wafer of silicon bonded to the first wafer of silicon, the second wafer of silicon defining a top wall of the primary channel.

In some embodiments, the shaft is coated in titanium nitride.

In some embodiments, the apparatus may further include a plurality of shafts, wherein each of the plurality of shafts has an exterior surface that is electrically conductive, wherein each of the plurality of shafts is electrically coupled to each other of the plurality of shafts, wherein each of the plurality of shafts extend from a proximal end to a distal end, each of the plurality of shafts defining a primary channel interior to the corresponding shaft extending from the proximal end toward the distal end, wherein the primary channel is open at the proximal end and closed at the distal end, wherein each of the plurality of shafts further defines one or more microchannels, wherein each of the one or more microchannels extends from the primary channel through a wall of the corresponding shaft, wherein each of the one or more microchannels has a diameter less than 1,000 micrometers.

In some embodiments, the apparatus may further include a plurality of electrodes, wherein each of the plurality of electrodes is electrically coupled to each other of the plurality of electrodes, wherein the plurality of electrodes are disposed adjacent to the plurality of shafts such that, when a voltage is applied between the plurality of shafts and the plurality of electrodes, an electric field is created perpendicular to an axis of each of the plurality of shafts.

In some embodiments, the apparatus may further include an electrode that is electrically isolated from the shaft, wherein the electrode is disposed adjacent to the shaft such that, when a voltage is applied between the shaft and the electrode, an electric field is created perpendicular to an axis of the shaft.

In some embodiments, the apparatus may further include drugs disposed in the primary channel.

In some embodiments, the apparatus may further include a syringe, wherein the syringe is fluidically to the primary channel.

In some embodiments, the apparatus may further include a handpiece removably mechanically coupled to the shaft.

According to one aspect of the disclosure, a method of manufacturing an apparatus, the method comprising creating a primary channel in a first silicon wafer with use of photolithography, wherein the primary channel has a depth of at least 10 micrometers and a length of at least 5 millimeters; bonding a second silicon wafer to the first silicon wafer after creation of the primary channel; etching the second silicon wafer to create one or more microchannels, wherein each of the one or more microchannels extends from the primary channel through the second silicon wafer, wherein each of the one or more microchannels has a diameter less than 1,000 micrometers.

In some embodiments, etching the second silicon wafer comprises etching the second silicon wafer with deep reactive ion etching.

In some embodiments, the method may further include depositing a coating of titanium nitride on at least one surface of the first silicon wafer or of the second silicon wafer.

According to one aspect of the disclosure, a method of delivering drugs, the method comprising inserting a shaft into a patient, the shaft extending from a proximal end to a distal end, the shaft defining a primary channel interior to the shaft extending from the proximal end toward the distal end, wherein the primary channel is open at the proximal end and closed at the distal end, wherein the shaft further defines one or more microchannels, wherein each of the one or more microchannels extends from the primary channel through a wall of the shaft, wherein each of the one or more microchannels has a diameter less than 1,000 micrometers; inserting an electrode into the patient adjacent to the shaft; and applying a voltage across the electrode and the shaft to create nanopores in at least some cells disposed between the shaft and the electrode.

In some embodiments, the shaft has a length of at least one millimeter.

In some embodiments, the method may further include moving a plunger of a syringe to cause the drugs to flow from the primary channel, through the one or more microchannels, and out of the shaft.

In some embodiments, applying a voltage across the electrode and the shaft comprises applying two or more pulses of voltage across the electrode and the shaft, wherein each of the two or more pulses are less than 2,000 milliseconds.

In some embodiments, the shaft is mechanically coupled to a handpiece, the method further comprising removing the shaft from the patient; and detaching the handpiece from the shaft.

BRIEF DESCRIPTION OF THE DRAWINGS

The detailed description particularly refers to the following figures, in which:

FIGS. 3A-3G are cross-section views of various embodiments of the needle of FIG. 2A;

FIGS. 7A-7G are various embodiments of an array of needles with microchannels next to an array of electrodes;

DETAILED DESCRIPTION

Figures 1, 2A, 2B:
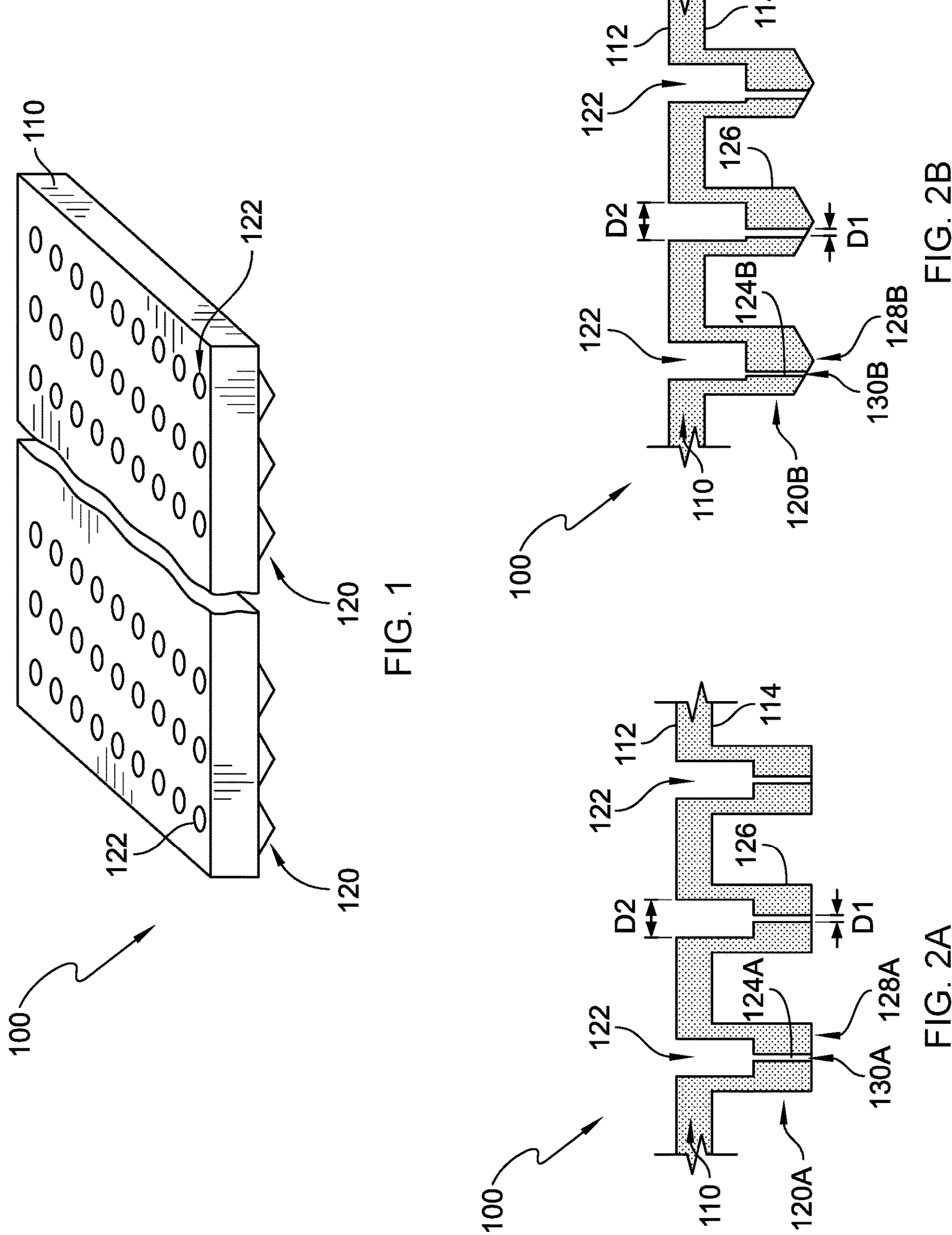
FIG. 1 is a schematic diagram showing one embodiment of a microstructure array that has a plurality of microstructures for delivering an agent to a target cell layer.
FIG. 2A is a schematic diagram showing one embodiment of a microstructure array that has a plurality of microstructures with blunt tips.
FIG. 2B is a schematic diagram showing one embodiment of a microstructure array that has a plurality of microstructures with pointed tips.

Terms used throughout this application are to be construed with ordinary and typical meaning to those of ordinary skill in the art. However, Applicant desires that the following terms be given the particular definition as defined below.

As used in the specification and claims, the singular form "a," "an," and "the" include plural references unless the context clearly dictates otherwise. For example, the term "a cell" includes a plurality of cells, including mixtures thereof.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

An "effective amount" is an amount sufficient to effect beneficial or desired results. An effective amount can be administered in one or more administrations, applications or dosages. The term "carrier" or "pharmaceutically acceptable carrier" means a carrier or excipient that is useful in preparing a pharmaceutical or therapeutic composition that is generally safe and non-toxic, and includes a carrier that is acceptable for veterinary and/or human pharmaceutical or therapeutic use. As used herein, the terms "carrier" or "pharmaceutically acceptable carrier" encompasses can include phosphate buffered saline solution, water, emulsions (such as an oil/water or water/oil emulsion) and/or various types of wetting agents. As used herein, the term "carrier" encompasses any excipient, diluent, filler, salt, buffer, stabilizer, solubilizer, lipid, stabilizer, or other material well known in the art for use in pharmaceutical formulations and as described further below.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

The terms "therapeutically effective amount" or "therapeutically effective dose" refer to the amount of a composition, such as glucose-modified insulin bound to a glucose-binding structure, that will elicit the biological or medical response of a tissue, system, animal, or human that is being sought by the researcher, veterinarian, medical doctor or other clinician over a generalized period of time. In some instances, a desired biological or medical response is achieved following administration of multiple dosages of the composition to the subject over a period of days, weeks, or years.

The term "subject" or "recipient" is defined herein to include animals such as mammals, including, but not limited to, primates (e.g., humans), cows, sheep, goats, horses, dogs, cats, rabbits, rats, mice and the like. In some embodiments, the subject is a human.

The terms "treat," "treating," "treatment," and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

A microstructure array and methods of using the same disclosed herein are useful in transporting an agent into or across a biological barrier (e.g., the cell membrane). The microstructure array disclosed herein has the ability to deliver the agent to a specific layer of cells within a tissue. As described in detail below, the microstructure array includes a plurality of microstructures that is configured to penetrate a barrier (e.g., a biological barrier layer). Each microstructure includes one or more delivery channels that is adapted to deliver agents via the one or more channels to reach an environment surrounding the microstructure (e.g., a particular layer of cells within tissue). In some embodiments, one or more microstructures of the microstructure array may include multiple delivery channels to allow agents to be delivered to multiple layers of cells within tissue simultaneously (or sequentially). In such embodiments, the one or more microstructures may have multiple delivery channels exiting from an angled microstructure that allow for different heights of the delivery channels within the microstructure. When the microstructure penetrates tissue, the delivery channels are positioned within different layers of cells and can therefore deliver agents at the different layers or levels within the tissue. It should be appreciated that the microstructure array may be used on the skin (or parts thereof), across the blood-brain barrier, mucosal tissue (e.g., oral, nasal, ocular, vaginal, urethral, gastrointestinal, respiratory), blood vessels, lymphatic vessels, cell membranes (e.g., for the introduction of material into the interior of a cell or cells), or other biological barrier. The biological barriers may be in humans or other types of animals, as well as in plants, insects, or other organisms, including bacteria, yeast, fungi, and embryos. Additionally, the microstructure array may be applied to tissue internally with the aid of a catheter or laparoscope. For certain applications, such as for a drug delivery to an internal tissue, a device with the microstructure array may be surgically implanted.

As illustrated in FIG. 1, a microstructure array 100 for transportation of an agent to a subject includes a planar base 110 having a top surface 112 and a bottom surface 114 opposite the top surface 112 and a plurality of microstructures 120 projecting outwardly from the bottom surface 114 of the planar base 110. In use, the microstructure array 100 is positioned relative to the subject, such that the bottom surface 114 of the planar base 110 faces toward the subject. Subsequently, the plurality of microstructures 120 on the bottom surface 114 is used to penetrate or puncture a barrier of the subject. To deliver the target agent to the subject, each microstructure 120 includes a body 126, a reservoir 122, and one or more delivery channels 124 defined within the body 126. Specifically, as shown in FIGS. 2A and 2B, the reservoir 122 extends inwardly from the top surface 112 of the planar base (102A in FIGS. 2A and 102B in FIG. 2B) and is configured to retain the target agent to be delivered to the subject. The delivery channel 124 is defined within the elongated body 126 that extends from the bottom surface 114 of the planar base (102A in FIGS. 2A and 102B in FIG. 2B) to a tip (128A in FIGS. 2A and 128B in FIG. 2B). The delivery channel (124A in FIGS. 2A and 124B in FIG. 2B) is adapted to act as a conduit between the reservoir 122 and the channel opening 130 to allow the target agent placed in the reservoir 122 to be delivered to the environment surrounding the microstructure (120A in FIGS. 2A and 120B in FIG. 2B) at the channel opening (130A in FIGS. 2A and 130B in FIG. 2B).

It should be appreciated that the microstructure array 100 may include the microstructures 120 that have different tips 128. It should be appreciated that a method of fabricating the microstructure array 100 is different depending on the type of tip 128 that the microstructure 120 has. Exemplary methods of fabricating the microstructure array 100 are described in FIGS. 3 and 4.

For example, as shown in FIG. 2A, the microstructure array 100 may include the microstructures 120A that have blunt tips 128A. In such an embodiment, the microstructure 120A has the reservoir 122 and the delivery channel 124A that extends from the center of the reservoir 122 to the channel opening 130A positioned at the center of the blunt tip 128A. A method of fabricating the microstructure array 100 with the microstructure 120A is further described in FIG. 3. However, it should be appreciated that, in some embodiments, the channel opening 130A may be positioned off-center of the blunt tip 128A. Alternatively, as shown in FIG. 2B, the microstructure array 100 may include the microstructures 120B that may have pointed tips 128B. In such an embodiment, the microstructure 120B has the reservoir 122 and the delivery channel 124B that extends from off-center of the reservoir 122 to the channel opening 130B positioned at a slanted side of the pointed tip 128B.

A method of fabricating the microstructure array 100 with the microstructure 120B is further described in FIG. 4. However, it should be appreciated that, in some embodiments, the channel opening 130B may be positioned at the center of the pointed tip 128B. Alternatively, in other embodiments, the microstructure array 100 may include both types of microstructures 120A, 120B.

As described further below, each microstructure 120 may have a specific aspect ratio that enables the microstructure array 100 to transport a target agent from the reservoir 122 into or across a biological barrier to deeper cell layers via the delivery channel 124 without irreversibly disrupting the barrier function. As used herein, the aspect ratio is defined as the distance from the bottom surface 114 to the tip 128A, 128B divided by width of the body 126. In the illustrative embodiment, the microstructure 120 has a height longer than 150 μm and has an aspect ratio of over 3. In some embodiments, each microstructure 120 may be approximately 200-1000 μm in height and have a delivery channel 124 that is 50-5000 nm in diameter.

Additionally, the delivery channel 124 has a diameter D1 smaller than the diameter D2 of the reservoir 122. For example, the diameter D1 of the delivery channel 124 is less than about 5000 nm, and the diameter D2 of the reservoir 122 is about 25 μm. In the illustrative embodiment, the microstructure 120 has a cylindrically shaped body. However, it should be appreciated that, in some embodiments, the elongated body 126 may be in any shape, such as a ridge, a herringbone pattern, a waveform pattern, cones, pyramids, or a combination thereof. It should be appreciated that, in some embodiments, the microstructure 120 may include multiple delivery channels 124. In such embodiments, the multiple delivery channel 124 may have the same height to allow the agents to be delivered to a targeted layer of cells within the tissue simultaneously or sequentially. Alternatively, in other embodiments, the multiple delivery channels 124 of the microstructure may have different heights that are to be positioned within different layers of cells and may therefore deliver agents at the different layers or levels within the tissue.

In some embodiments, the delivery channel 124 may be defined by a first channel and a second channel that are connected at a junction. Specifically, the first channel extends from the channel opening toward the junction, and a second channel extends from the junction toward the reservoir 122, such that the first and second channels are in fluid communication with the reservoir 122. As discussed further below, the first channel has an inner diameter that is smaller than an inner diameter of the second channel. For example, in the illustrative embodiment, the inner diameter of the first channel is less than about 5000 nm and the inner diameter of the second channel is about 5-20 μm.

In the illustrative embodiment, the reservoir 122 is integrated with the planar base 102 and is sized to feed a single microstructure 120. However, in some embodiments, the reservoir 122 may be sized to feed more than one microstructure 120. For example, in such embodiments, the microstructure array 100 may include a single large reservoir to feed the plurality of the microstructures 120 of the microstructure array 100. It should be appreciated that, in some embodiments, the reservoir 122 may be fabricated separately and interfaced with the planar base 102. In one embodiment, the reservoir 122 may include a porous material, wherein the agent to be administered is stored in pores of the porous material. In another embodiment, the reservoir is sealed. In one variation of this embodiment, the microstructure array further includes at least one puncturing barb extending from the first surface of the planar substrate, wherein the puncturing barb may be used to puncture the sealed reservoir.

The reservoir 122 is adapted to contain any agent that is to be delivered to a targeted cell layer through the delivery channel 124 of the microstructure 120 via a release mechanism. The agent to be delivered across a barrier layer may be selected from a group comprising peptides, proteins, carbohydrates, nucleic acid molecules, lipids, organic molecules, biologically active inorganic molecules, and combinations thereof. For example, a wide range of drugs may be formulated for delivery with the microstructure array 100.

As used herein, the terms "drug" or "drug formulation" are used broadly to refer to any prophylactic, therapeutic, diagnostic, or theranostic agent, or other substance that may be suitable for introduction to biological tissues, including pharmaceutical excipients and substances for tattooing, cosmetics, and the like. The drug can be an agent having biological activity. The drug formulation may include various forms, such as liquid solutions, gels, solid particles (e.g., microparticles, nanoparticles), or combinations thereof. The drug may comprise small molecules, large (i.e., macro-) molecules, or a combination thereof. In representative, not non-limiting, embodiments, the drug can be selected from among amino acids, vaccines, antiviral agents, gene delivery vectors, interleukin inhibitors, immunomodulators, neurotropic factors, neuroprotective agents, antineoplastic agents, chemotherapeutic agents, polysaccharides, anti-coagulants, antibiotics, analgesic agents, anesthetics, antihistamines, anti-inflammatory agents, and viruses. The drug may be selected from suitable proteins, peptides and fragments thereof, which can be naturally occurring, synthesized or recombinantly produced. In one embodiment, the drug formulation includes insulin. The drug formulation may further include one or more pharmaceutically acceptable excipients, including pH modifiers, viscosity modifiers, and diluents.

In some embodiments, the agent may be an electrical stimulant. Pulsed electric fields have many applications, such as in regenerative medicine. In such embodiments, the microstructure array 100 may be used to deliver pulsed electric fields at different levels across a tissue thickness. In some embodiments, the reservoir 122 may include a means for producing an agent to be transported to the target recipient. For example, the reservoir 122 may contain cells that are capable of producing an agent to be administered or delivered to the recipient. The cells may be mammalian cells, such as human cells, or may be cells from any other source. For example, the cells may be pancreatic β cells or stem cell-differentiated human pancreatic cells.

The release mechanism may involve an electric field, a magnetic field, an electromagnetic filed, a pressure field, ultrasonic energy, tension, diffusion injection, osmosis, concentration gradient, vacuum, pressure, a mechanical force or sheer force, heat, a chemical reaction, or a combination thereof. For example, in use, the microstructure array 100 may be placed on a biological barrier layer, which allows the tips 128 of the microstructures 120 to penetrate the barrier layer and deliver agents received in the reservoirs 122 to the environment surrounding the channel openings 130 of the microstructures 120 (e.g., intracellular space) via the delivery channel 124. To do so, a porating electric field may be applied across the microstructure array 100 to disrupt or deform the biological barrier layer (e.g., cellular membranes) that allows the agents to be translocated into the cell. The strength of the electric field required for translocation may depend on the target tissue or system. Conversely, the agents may be drawn from an environment outside of the channel opening 130 through the delivery channel 124 and deposited in the reservoir 122 for feedback communication.

In the illustrative embodiment, the microstructure array 100 further includes first and second electrodes to create an electric field between the electrodes positioned at the opposite sides of the delivery channel 124 to enhance delivery of the agent. Specifically, the first electrode is in contact with the reservoir 122 and the second electrode is positioned at the distal tip 128 of the microstructure 120, such that the electric filed is generated and across the tissues between two electrodes. The voltage, frequency, and other electrical field parameters may be selected based on the distance between the electrodes.

The electrodes structures may be formed as concentric bands that are connected to conductive pads. Each band and banded segment may be wired together to an electroporation power supply or wired separately to an electroporation power supply and can be energized in a variety of geometric and timed patterns and arrangements. Moreover, the different bands and band segments may be maintained at different electrical potentials (voltages) with respect to the first electrode structure. An agent can be delivered through a channel opening 130 at the distal tip 128 so that it permeates through tissue outwardly in a region. The region can coincide with the electrical field being generated between first electrode structure and second electrode structure. It should be appreciated that the electrical field may enhance a cellular permeability, thus enhancing the delivery of the desired agent to the cells.

The microstructure array capable of electroporation may include an alternating current (AC) power supply adapted to deliver electroporation current to the electrode structures at a desired voltage and frequency, typically selected to deliver electroporation current to the electrodes at a voltage in the range from 0.1 V to 30 kV. In some cases, the voltage is less that about 50 to 500V. The particular voltage will depend at least in part on the spacing between the first and second electrode structures. The frequency will typically be in the range from 10 Hz to 107 Hz, usually from 104 Hz to 106 Hz. The current can be applied at pulsed intervals, such as every 1, 2, 3, 4, 5, 6, 7, 8, 9, 10, 11, 12, 13, 14, 15, 16, 17, 18, 19, 20, or more milliseconds, and any amount of pulses, such as 1, 2, 3, 4, 5, 6, 7, 8, 9, 10, 11, 12, 13, 14, 15, 16, 17, 18, 19, 20, or more pulses, can be applied in a given interval. The intervals can be repeated until the desired result is achieved.

It should be appreciated that the reservoir 122 may include a feedback component to alter a volume or an amount of the agent to be transported across the biological barrier based on a physiological signal. To do so, the feedback component may include a switch that is adapted to control the release mechanism to release an agent to a target recipient based on a detection or absence of a signal. For example, the agent may be contained in the reservoir 122 (i.e., not released into the delivery channel 124) until the signal is detected. Upon a detection of the signal, the agent is released to the target recipient. For example, the feedback component may detect a presence of a pathogen in a subject, and when the pathogen is detected, the feedback component allows a release of an agent from the reservoir. Alternatively, the detection of a signal may have an opposite effect. In such example, the reservoir defaults to delivery of an agent to the target recipient, unless a signal is detected, which causes the reservoir 122 not to release the agent for delivery to the recipient.

In some embodiments, the feedback component may detect changes in a physiological signal (e.g., pH or temperature). For example, the feedback component may determine whether to release the agent or may change the volume or amount of agent to be released or administered to the target recipient in response to determination that the physiological signal has changed by a predefined amount or reached a predefined numerical value. Additionally or alternatively, the feedback component may also adjust the amount or volume of the agent to be released based on an amount of signal detected. For example, a greater amount of signal detected may result in a greater amount of agent released, or conversely, a greater amount of signal detected may result in a smaller amount of agent released. It should be appreciated that the detected physiological signal may indicate a presence of a substance in the target recipient to which the microstructure array is being administered. The physiological signal may be generated naturally in the recipient or may be triggered by a non-endogenous or foreign substance. For example, the physiological signal may indicate an amount of the substance present in the target recipient, such as, but not limited to, glucose, cholesterol, bilirubin, creatine, metabolic enzymes, hemoglobin, heparin, clotting factors, uric acid, carcinoembryonic antigen or other tumor antigens, reproductive hormones, oxygen, alcohol, tobacco metabolites, and illegal drugs.

In some embodiments, the reservoir 122 may be semi-permeable to allow the exchange of fluid with the target recipient. This, in turn, allows the feedback component to be in fluid communication with the target recipient and thereby detect changes in the physiological signal of the recipient. For example, the reservoir 122 may contain cells that are sensitive to changes in a physiological signal from the recipient. Such physiological changes in the recipient can stimulate the cells to release an agent, or to stop releasing an agent, as described above in regard to the feedback component. In one example, the semi-permeable reservoir may be made of an alginate microgel.

In the illustrative embodiment, the agent in the reservoir to be delivered to the target recipient may be a therapeutic, prophylactic, diagnostic, or theranostic substance. Additionally, more than one agent may be delivered at a time. Additionally or alternatively, different agents may be delivered sequentially or simultaneously through different channels at a same time. It should be appreciated that, in the embodiments where multiple delivery channels 124 reach different layers of cells, different agents may be administered to different strata of cells within tissue simultaneously utilizing the microstructure array disclosed herein. Specifically a first agent may be delivered via a first delivery pathway to a first layer of cells, and a second agent may be delivered via a second delivery pathway to a second layer of cells.

Referring now to FIG. 3, a method for creating a microstructure array 100 that has a plurality of microstructures 120A with blunt tips 128A using semiconductor manufacturing techniques such as photolithographic and etching techniques is shown. The method begins by creating the reservoir 122 on a wafer 140. In the illustrative embodiment, the wafer 140 has a height D7 greater than 300 μm and is made of silicon and the oxide layer 150 is made of silicon dioxide or other oxide. However, it should be appreciated that, in some embodiments, the wafer 140 may be made of other substrate, such as glass, silicon carbide, plastic, polymer and metals.

Figures 3A, 3B, 3C:
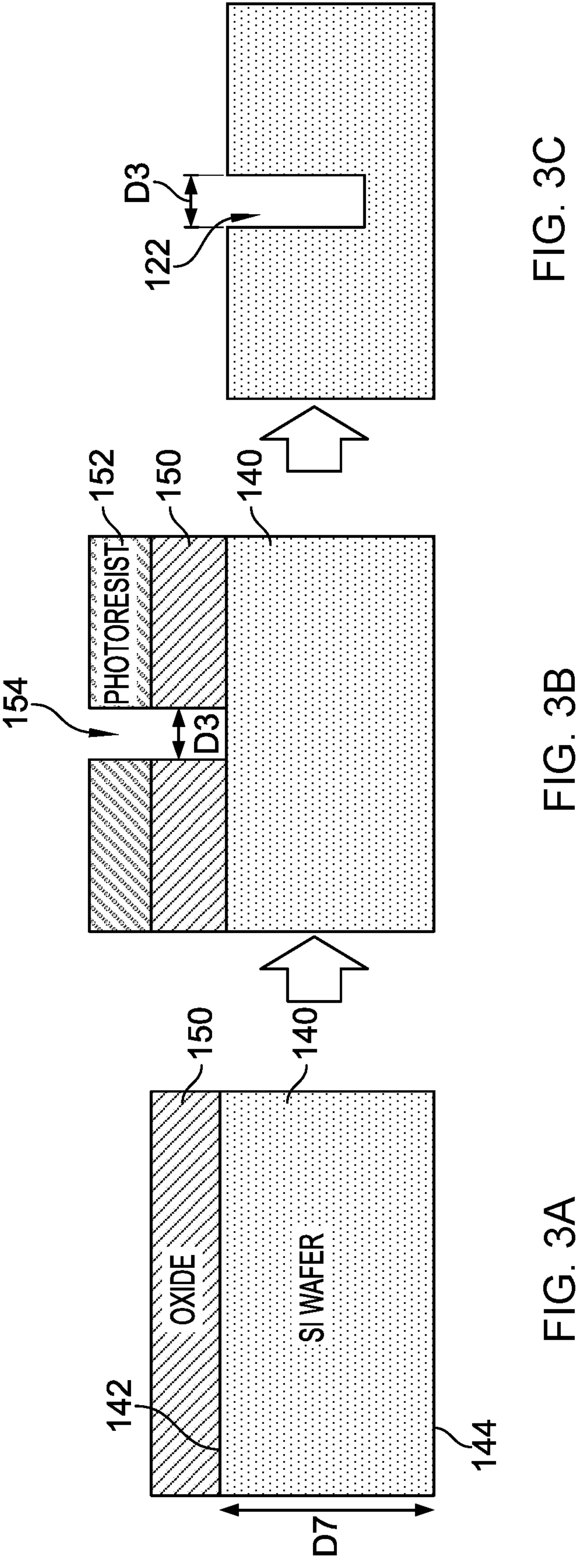
FIGS. 3A-3G are schematic diagrams illustrating a method of fabricating a microstructure array of FIG. 2A using semiconductor process such as lithography and etching techniques.

As illustrated in FIG. 3A, an oxide layer 150 is deposited on the first surface 142 of the wafer 140 using an oxidation process. The oxidation process may include chemical vapor deposition or wet oxidation at high temperature. Chemical vapor deposition is a preferred method because it is cost-effective, can be performed at low temperature and has fast deposition rate compared to wet oxidation, which requires high-temperature (over 1,000° C.) and has slow growth rate. A photoresist material 152 is then deposited on top of the oxide layer 150 by spin coating and is exposed by UV light in an optical lithography tool with a photomask (not shown) to define a pattern (e.g., arrays of holes) 154 in the photoresist material layer 152, as illustrated in FIG. 3B. In the illustrative embodiment, each hole 154 defined in the photoresist layer 152 has a diameter D3 of about 10 to 30 μm and is used as a mask to etch through the oxide layer 150. For example, a plasma etching (e.g., using fluorine containing plasma gas) may be performed to generate a mask that is to be used to create the reservoirs 122 of the microstructure array 100. Once the mask is created, the remaining photoresist material 152 is removed. Subsequently, the wafer 140 is etched using the arrays of hole pattern 154 in the oxide layer 150 to create hollow channels (i.e., the reservoirs 122) in the wafer 140 and the oxide layer 150 is removed, as illustrated in FIG. 3C. In the illustrative embodiment, each reservoir 122 has an initial diameter D3 of about 10 to 30 μm. However, as described further below in FIG. 3G, the diameter of the hollow reservoirs 122 may be further adjusted.

Figures 3D, 3E, 3F, 3G:
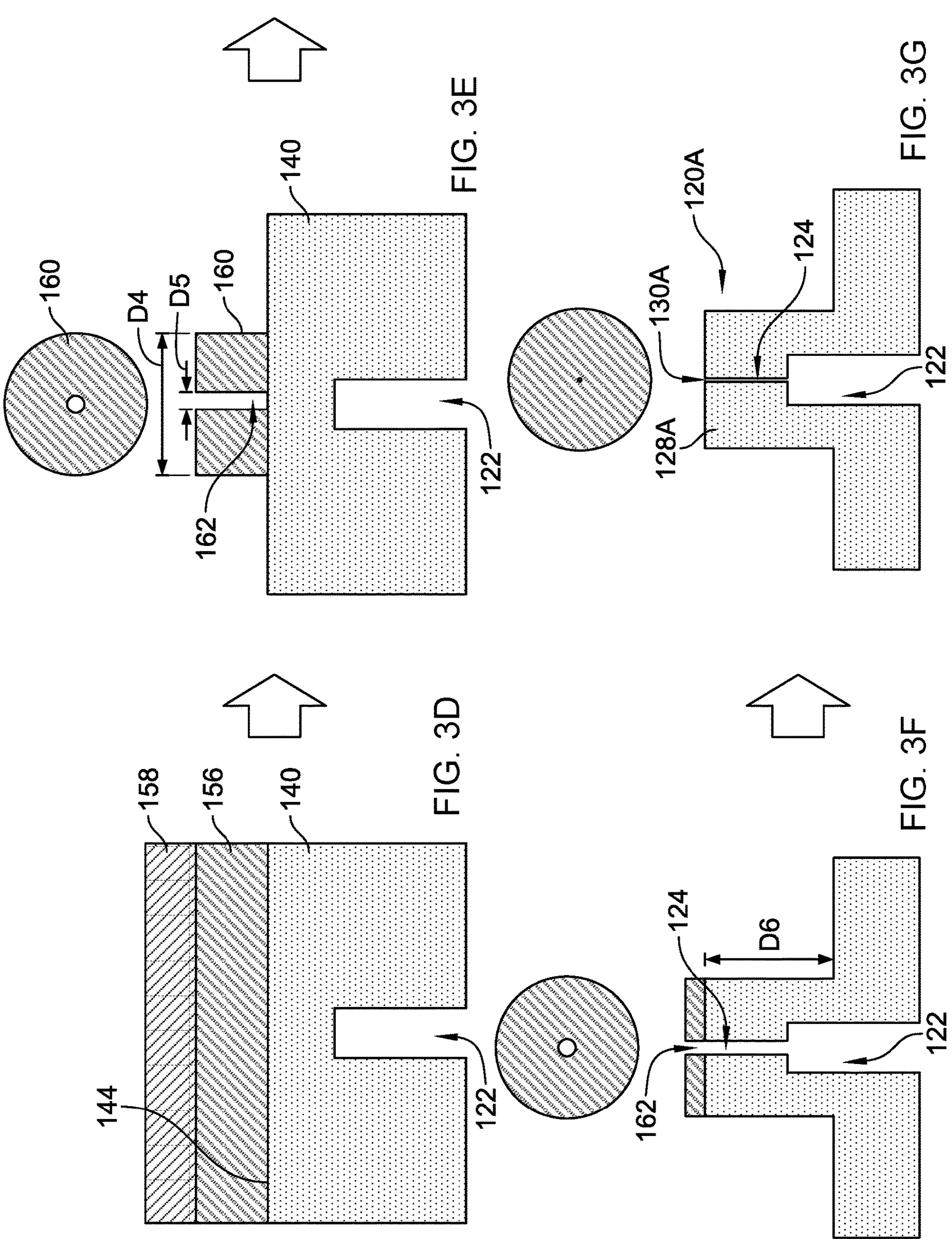

Subsequently, the delivery channels 124 are formed in the wafer 140 to create the microstructure array 100. To do so, as illustrated in FIG. 3D, an oxide layer 156 is deposited on the second surface 144 of the wafer 140 using the oxidation process (e.g., chemical vapor deposition or wet oxidation at high temperature). The photoresist material 158 is then deposited on the oxide layer 156 by spin coating and is exposed by UV light in an optical lithography tool with a photomask (not shown) to define a disk-shape in the photoresist layer 158 that aligns with each reservoir 122. In the illustrative embodiment, each disk-shaped photoresist layer (not shown) has a diameter D4 of about 50 μm and is used as a mask to etch through the oxide layer 156 to generate a disk-shaped oxide layer 160 that has a diameter D4 of about 50 μm. Subsequently, as illustrated in FIGS. 3E and 3F, a similar lithography patterning and etching process is repeated to create a narrow channel 162 in the center of each disk-shaped oxide layer 160. In the illustrative embodiment, the hole in the oxide layer 162 has a diameter D5 of about 0.05 μm to 5 μm and is used to define the delivery channel 124 of each microstructure 120.

Each disk-shaped oxide layer 160 is then used to etch through the wafer 140 to form an outline of the blunt microneedle tip 128A with the delivery channel 138. The delivery channel 124 extends from the opening 130A at the blunt microneedle tip 128A through the center of the microstructure 120A to the reservoir 122, as illustrated in FIG. 3F. For example, an etching process is performed using a highly anisotropic deep reactive ion etch (DRIE) to drill hollow channels 124 through the wafer 140. It should be appreciated that, in some embodiments, the delivery channel 138 may be positioned off-centered in the microstructure 120.

Subsequently, the disk-shaped oxide layer 160 is removed and the wafer 140 is cleaned. In the illustrative embodiment, the resulting microstructure 120A has a length D6 greater than 150 μm with a delivery channel 130A that has an initial diameter of about 2 to 10 μm. Etching a narrow delivery channel with extremely high aspect ratio is difficult via conventional dry etching techniques. Instead, in some embodiments, a hollow channel is etched with a larger inner diameter, then the inner diameter is shrunk to a target size by depositing oxide, silicon, or nitride films on the surface, as illustrated in FIG. 3G. Those materials can be deposited by chemical vapor deposition or atomic layer deposition techniques that can conformally coat the structured surface, thereby shrinking the diameter of the delivery channel but increasing the outer size of the microneedle. In the illustrative embodiment, the target diameter of the delivery channel 138 is 0.05-5 μm. The diameter of the reservoir is around 10-30 μm.

Referring now to FIG. 4, a method for creating a microstructure array 100 that has microstructures 120B with sharp tips 128B using photolithographic and etching techniques is shown. The method begins by creating the reservoir 122 on a wafer 140. In the illustrative embodiment, the wafer 140 has a height D7 greater than 300 μm and is made of silicon and the oxide layer 150 is made of silicon dioxide or other oxides. However, it should be appreciated that, in some embodiments, the wafer 140 may be made of other substrate, such as glass, silicon carbide, plastic, polymer, and metals.

Figures 4A, 4B, 4C:
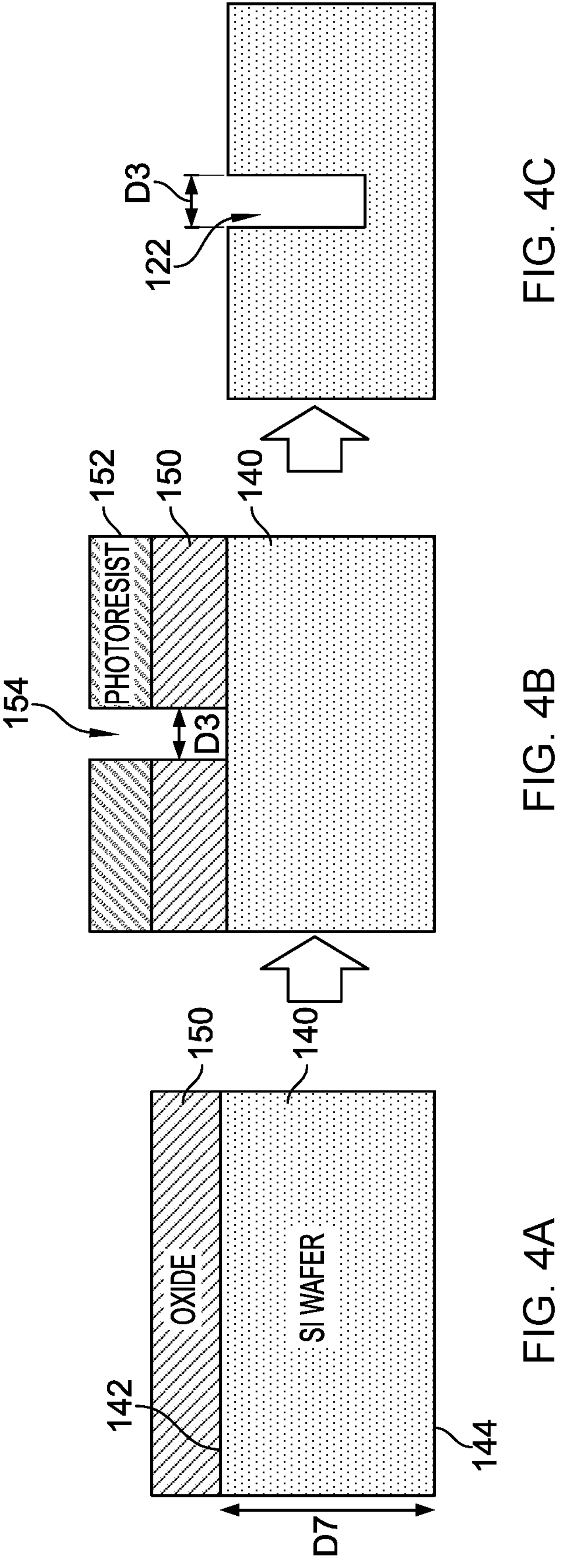
FIGS. 4A-4K are schematic diagrams illustrating a method of fabricating a microstructure array of FIG. 2B using semiconductor process such as lithography and etching techniques.

As illustrated in FIG. 4A, an oxide layer 150 is deposited on the first surface 142 of the wafer 140 using an oxidation process. The oxidation process may include chemical vapor deposition or wet oxidation at high temperature. Chemical vapor deposition is a preferred method. A photoresist material 152 is then deposited on top of the oxide layer 150 by spin coating and is exposed by UV light in an optical lithography tool with a photomask (not shown) to define a pattern (i.e., arrays of holes) 154 in the photoresist material layer 152, as illustrated in FIG. 4B. In the illustrative embodiment, each hole 154 defined in the photoresist layer 152 has a diameter D3 of about 10 to 30 μm and is used as a mask to etch through the oxide layer 150. For example, a plasma etching (e.g., using fluorine containing plasma gas) may be performed to generate a mask that is to be used to create the reservoirs 122 of the microstructure array 100. Once the mask is created, the remaining photoresist material 152 is removed. Subsequently, as illustrated in FIG. 4C, the wafer 140 is etched using the arrays of hole pattern 154 in the oxide layer 150 to create hollow channels (i.e., the reservoirs 122) in the wafer 140 and the oxide layer 150 is removed. In the illustrative embodiment, each reservoir 122 has an initial diameter D3 of about 10 to 30 μm. However, as described further below in FIG. 4K, the diameter of the hollow reservoirs 122 may be further adjusted.

Figures 4D, 4E, 4F, 4G:
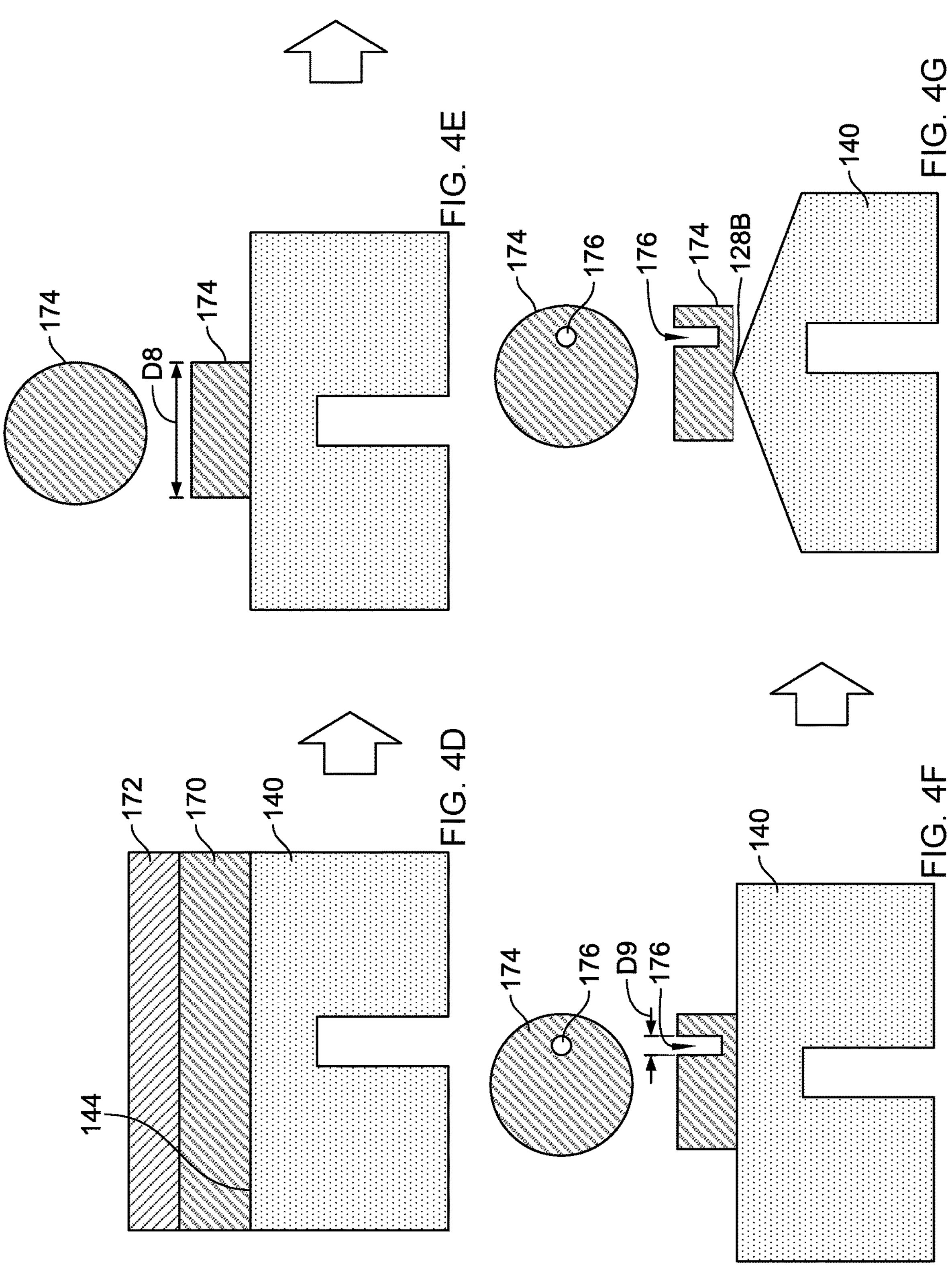

Subsequently, the delivery channels 124 are formed in the wafer 140 to create the microstructure array 100. To do so, as illustrated in FIG. 4D, an oxide layer 170 is deposited on the second surface 144 of the wafer 140 using the chemical vapor deposition (e.g., chemical vapor deposition or wet oxidation at high temperature). The photoresist material 172 is then deposited on the oxide layer 170 by spin coating and is exposed by UV light in an optical lithography tool with a photomask (not shown) to define a disk-shape in the photoresist layer that aligns with each reservoir 122, as illustrated in FIG. 4E. In the illustrative embodiment, each disk-shaped photoresist layer has a diameter of about 50 μm and is used as a mask to etch through the oxide layer 170 to generate an oxide disk 174 that has a disk-shape and has a diameter D8 of about 50 μm. Subsequently, as illustrated in FIG. 4F, a similar lithography patterning and etching process is repeated to create a hollow cavity 176 in each oxide disk 174. In the illustrative embodiment, the hollow cavity 176 has a diameter D9 of about 0.1 μm to 5 μm and is used to define the delivery channel 138 of each microstructure 120.

Figures 4H, 4I, 4J, 4K:
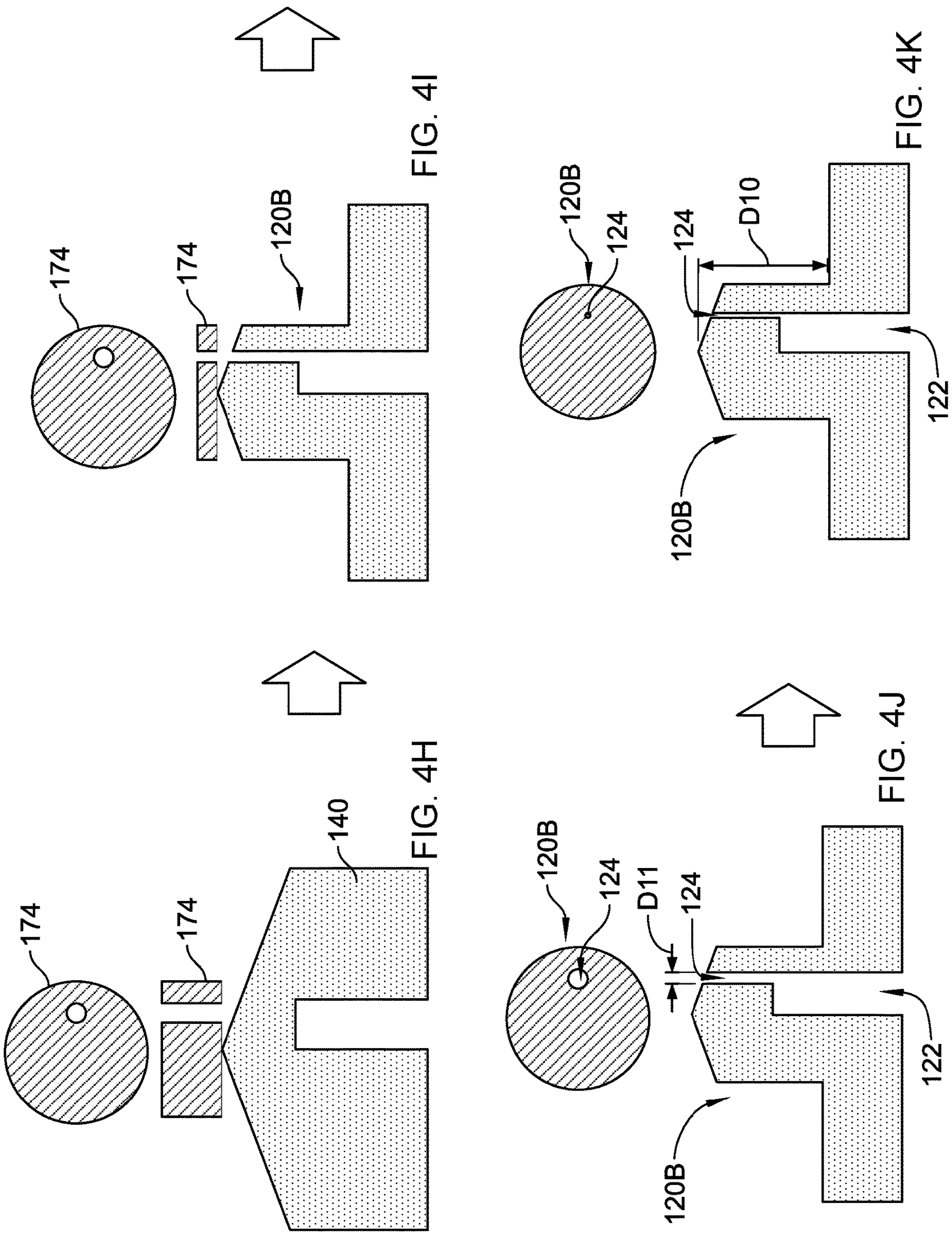

Each oxide disk 174 is then used to etch through the wafer 140 to form a pointed microneedle tip 128B of the microstructure 120B via isotropic silicon etching, as illustrated in FIG. 4G. Once the pointed microneedle tip 128B is established, the hollow cavity 176 of the oxide disk 174 is further etched until the hollow cavity 176 punches through the rest of the oxide disk 174, as shown in FIG. 4H. Subsequently, the wafer 140 is further etched to form an outline of the microstructure 120B with the delivery channel 124 that extends from the microneedle tip 128 through the microstructure 120 to the reservoir 122, as illustrated in FIG. 4I.

Subsequently, as shown in FIG. 4J, the oxide disks 172 are removed and the wafer 140 is cleaned. In the illustrative embodiment, the resulting microstructure 120B has a length D10 greater than 150 μm with the delivery channel 124 that has an initial diameter D11 of about 0.1 to 5 μm. To further decrease the size of the diameter of the delivery channel 124 to a target size of 0.05-5 μm, an oxide, silicon, or nitride layer may be deposited on the microstructure array 100, as illustrated in FIG. 4K. As described above, such a shrinking process may also decrease the diameter of the reservoir 122 to a target size. In the illustrative embodiment, the target diameter of the delivery channel 124 is 0.05-5 μm.

Figure 5:
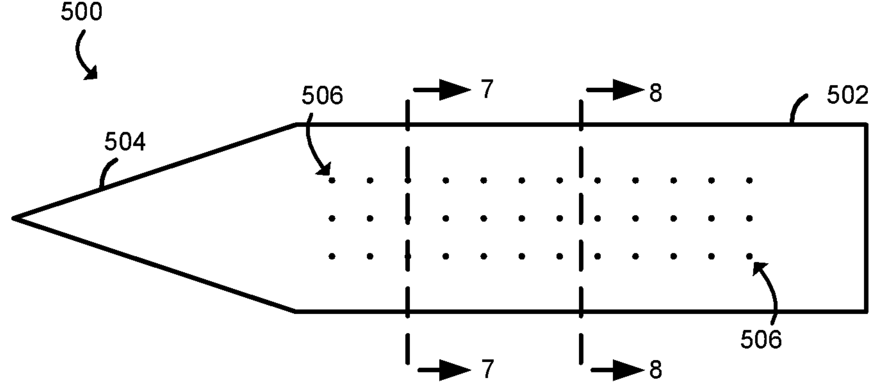
FIG. 5 is a top-down view of one embodiment of a needle with microchannels.

Referring now to FIG. 5, in the illustrative embodiment, a needle 500 is formed from silicon. In some embodiments, the needle 500 may be formed from a different material, such as stainless steel or plastic. The needle 500 has a shaft 502 and a tip 504. The needle 500 has one or more primary channels 702 (see FIGS. 7A-7G) running along the interior of the shaft. The needle 500 has several microchannels 506 extending from the one or more primary channels 702 to a surface of the needle 500. Each of the illustrative microchannels 506 has a diameter of approximately 4 micrometers. In use, the needle 500 may be inserted into a patient, such as through the skin or into organs. A drug may be administered by allowing it to flow from a primary channel 702 into the patient through the microchannels 506. In embodiments with multiple primary channels 702, different dugs may be administered into different primary channels 702. In some embodiments, an electric field may be applied to cause electroporation of tissue cells and facilitate the flow of the drug to the desired location. In those embodiments, the needle 500 may be coated with an electrically conductive coating, such as titanium nitride or other biocompatible material. Additionally or alternatively, in some embodiments, an electrode may be in contact with the drug, and the drug itself may propagate with the electric field by electrophoresis. In some embodiments, instead of delivering drugs, one of the primary channels 702 and corresponding microchannels 506 may be used to extract a sample from a patient, such as extracellular fluid, vesicles, etc., or the needle 500 may integrate devices for monitoring tissue environment such as temperature, pH, etc.

It should be appreciated that the width of the microchannels 506 may be varied such that certain drugs, such as genes, DNA, or protein, can be administered at a desired rate. Additionally, the drugs may be administered to a variety of different depths, based on the positioning of the microchannels 506. In the illustrative embodiment, there is a single primary channel 702. Additionally or alternatively, in some embodiments, there may be more than one primary channel 702. It should be appreciated that the different primary channels 702 may have be used to deliver different drugs. In some embodiments, different microchannels 506 on the same needle 500 may have different diameters. For example, the microchannels 506 connected to one primary channel 702 may have a different diameter as compared to microchannels 506 connected to a second primary channel 702.

The drug may be inserted into the primary channel 702 in any suitable manner. For example, in the illustrative embodiment, the primary channel 702 may be connected to a syringe with use of a tube running from the syringe to a block (such as polydimethylsiloxane) that is coupled to an opening of the primary channel. In some embodiments, the syringe may be embedded in or form a part of a handpiece. The handpiece and syringe may be removably connected to the needle 500 such that the needle 500 may be discarded after a single use and the handpiece and syringe may be reused.

As for the microstructure array described above, it should be appreciated that the needle 500 with microchannels 506 may be used on the skin (or parts thereof), across the blood-brain barrier, mucosal tissue (e.g., oral, nasal, ocular, vaginal, urethral, gastrointestinal, respiratory), blood vessels, lymphatic vessels, cell membranes (e.g., for the introduction of material into the interior of a cell or cells), or other biological tissue or barrier. The biological barriers may be in humans or other types of animals, as well as in plants, insects, or other organisms, including bacteria, yeast, fungi, and embryos. Additionally, the needle 500 with microchannels 506 may be applied to tissue internally with the aid of a catheter, endoscope, laparoscope, etc. For certain applications, such as for a drug delivery to an internal tissue, a device with the needle 500 with microchannels 506 may be surgically implanted or integrated into surgical tools.

The illustrative needle 500 is approximately 10 millimeters long with a width of approximately 1 millimeter and a height of 0.5 millimeters. In other embodiments, the needle 500 may be any suitable length, such as 1-500 millimeters, and any suitable width and height, such as 0.1-5 millimeters. The illustrative primary channel 702 has a width of approximately 100 micrometers and a height of approximately 100 micrometers. In some embodiments, the primary channel 702 may have different dimensions, such as a width and/or height of 10 to 5,000 micrometers. The microchannels 506 may have a diameter different from the illustrative diameter of 4 micrometers, such as a diameter of 0.1-500 micrometers.

The illustrative needle 500 is formed from silicon with use of conventional semiconductor processes such as photolithography, wafer bonding, etching, etc., as discussed in more detail below in regard to FIGS. 8-14. Additionally or alternatively, the needle 500 may be formed from any suitable material (such as stainless steel, plastic, glass, etc.) that is compatible with manufacturing techniques to form a needle 500 as described herein.

Figure 6:
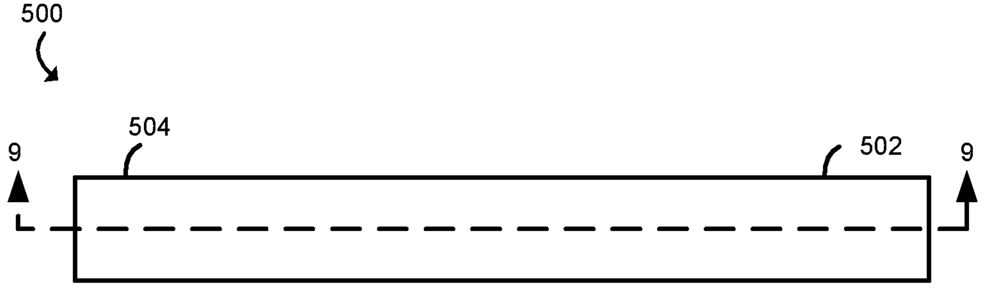
FIG. 6 is a side view of the needle of FIG. 5.
Figure 8:
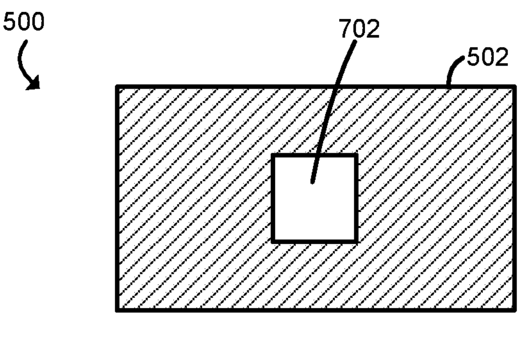
FIG. 8 is a cross-section view of the needle of FIG. 5.

Referring now to FIG. 6, a side view of the needle 500 shows that the needle 500 may have a uniform thickness. In some embodiments, the tip 504 of the needle may have a variable thickness, such as by coming to a point at the end of the tip 504.

Referring now to FIGS. 7A-7G, several cross-section views of the needle 500 are shown. In FIG. 7A, a single primary channel 702 is shown with the microchannels 506 extending from the primary channel 702 to a surface of the needle 500. In FIGS. 3B-3D, different configurations of the microchannels 506 are shown, such as microchannels 506 extending from the primary channel 702 to both a top and bottom surface of the needle 500 and/or microchannels 506 extending from the primary channel 702 to a side surface of the needle 500. In some embodiments, the needle 500 may include more than one primary channel 702, as shown in FIG. 7E. Each of the primary channels 702 may be used to deliver a different drug.

It should be appreciated that microchannels 506 may be arranged in different configurations that those shown in FIGS. 7A-7E. For example, in one embodiment shown in FIG. 7F, the needle 500 may have a circular shape with one primary channel 702 and several microchannels 506 extending radially from the center primary channel 702. In another embodiment shown in FIG. 7G, the needle 500 may have a circular shape with several primary channels 702, with each of the primary channels have one or more corresponding microchannels 506.

Figure 9A:
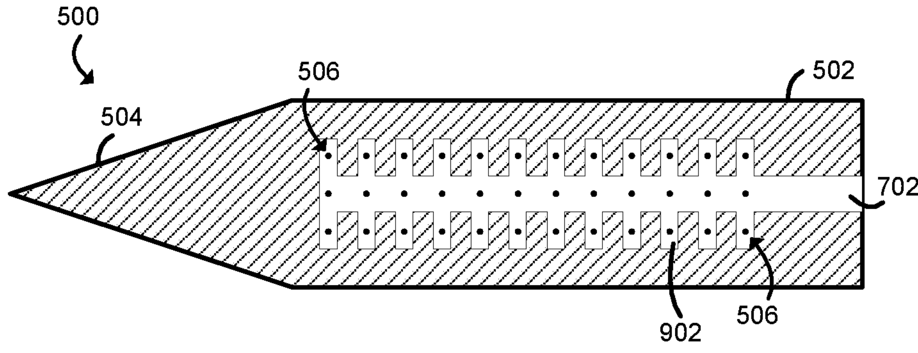
FIGS. 9A & 9B are cross-section views of various embodiments of the needle of FIG. 6.
Figure 9B:
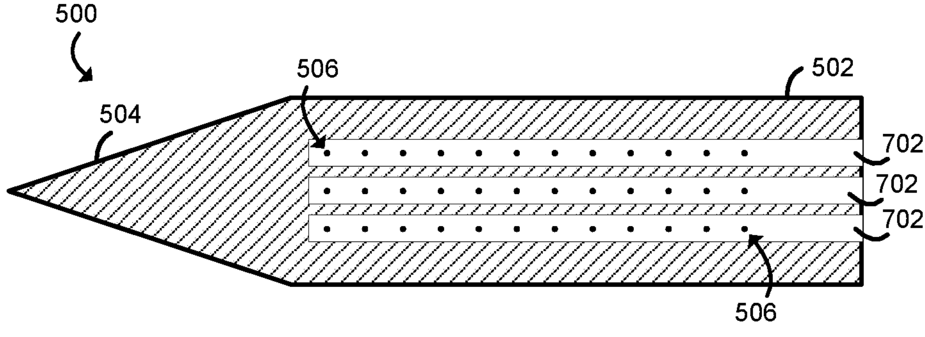

Referring now to FIGS. 9A & 9B, a top-town cross-section view of the needle 500 with one primary channel 702 is shown in FIG. 9A, and a top-down cross-section view of the needle 500 with several primary channels 702 is shown in FIG. 9B. It should be appreciated that, in some embodiments, the primary channel 702 may include one or more side channels 902 extending perpendicular to the primary channel 702. Some or all of the microchannels 506 may extend from the side channels 902 to the surface of the needle 500.

Figure 10:
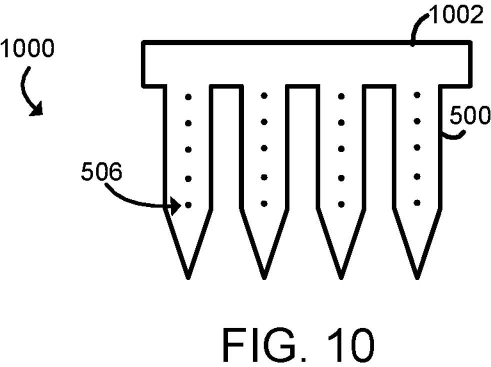
FIG. 10 is one embodiment of an array of needles with microchannels.

Referring now to FIG. 10, in some embodiments, two or more needles 500 may be joined together by an anchor 1002 to form array of needles 1000. Each of the needles 500 in the array of needles 1000 may have a primary channel 702 and one or more microchannels 506, as described in more detail above. In the illustrative embodiment, the needles may have a gap between them of 3 millimeters. In some embodiments, the gap may be larger or smaller, such as 0.1-50 millimeters.

Figure 11A:
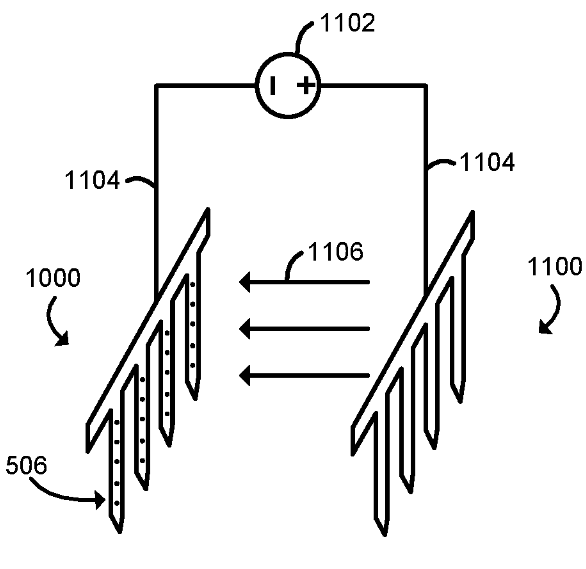

Referring now to FIG. 11A, in some embodiments, an array of needles 1000 may be disposed opposite an array of electrodes 1100. A voltage source 1102 (such as a battery) may be connected to the array of needles 1000 and the electrodes 1100, such as through a pair of wires 1104. The electrodes 1100 may be formed from any suitable material, such as a metal, silicon needles coated in biocompatible conductive materials such as titanium nitride similar to the array of needles 1000, etc. The array of needles 1000 and the array of electrodes 1100 may be spaced apart any suitable distance, such as 0.5 to 100 millimeters. It should be appreciated that, with a smaller spacing, a relatively low voltage may lead to a relatively large electric field.

In use, the array of needles 1000 and the array of electrodes 1100 may be inserted into a patient. The voltage source 1102 may apply a voltage across the array of needles 1000 and the array of electrodes 1100, creating an electric field 1106. The voltage applied may be any suitable voltage, such as 0.1-30,000 volts, with a corresponding electric field of, e.g., 1-1,000 volts per centimeter. In the illustrative embodiment, the electric field 1106 may cause electroporation in some or all of the cells in the area of the electric field, temporarily creating nanopores in the cells and causing the drug to flow into the cells by, e.g., electrophoresis or diffusion or fluidic force. In some embodiments, the electric field 1106 may be pulsed. For example, in the illustrative embodiment, the electric field 1106 may be applied in ten pulses of 100 milliseconds for each pulse. In some embodiments the pulses may have a different amplitude. For example, the amplitude of each pulse may be lower than that of the previous pulse. The pulses may be applied for any suitable length of time, such as 10-1,000 milliseconds, and may be repeated for any suitable number of times, such as 1-30 times, and may have any suitable time between pulses, such as 10-1,000 milliseconds. It should be appreciated that, in some embodiments, the voltage source 1102 may apply a reverse voltage, reversing the direction of the electric field 1106.

Figure 11B:
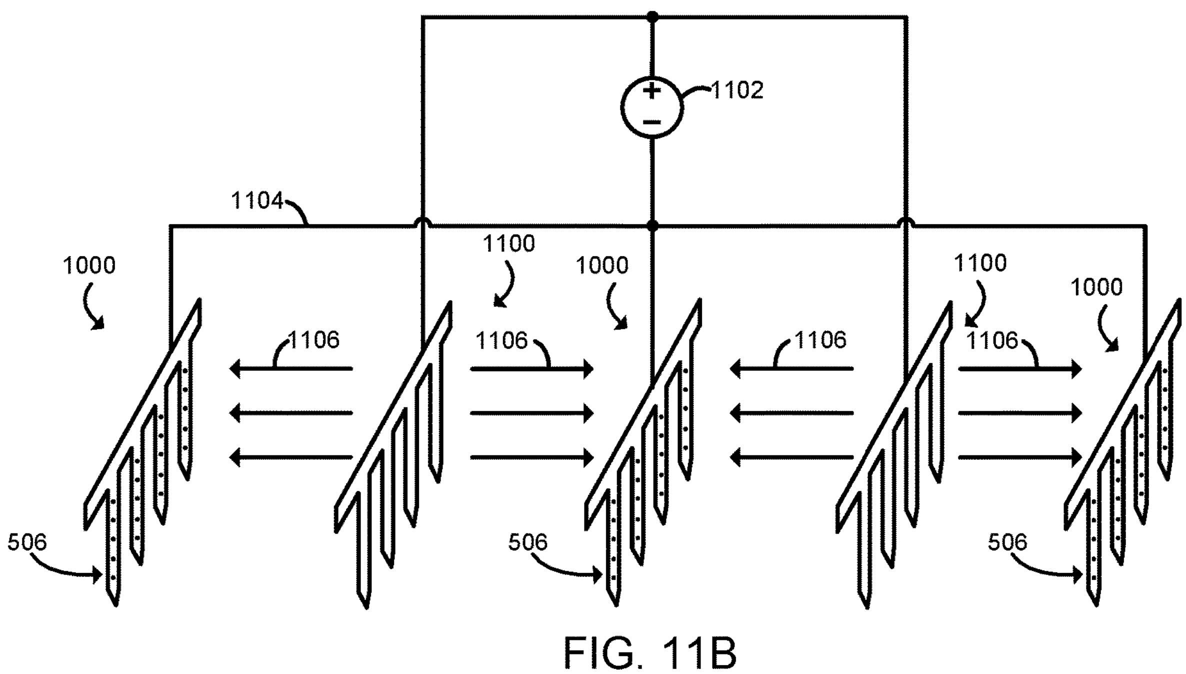
Figure 11C:
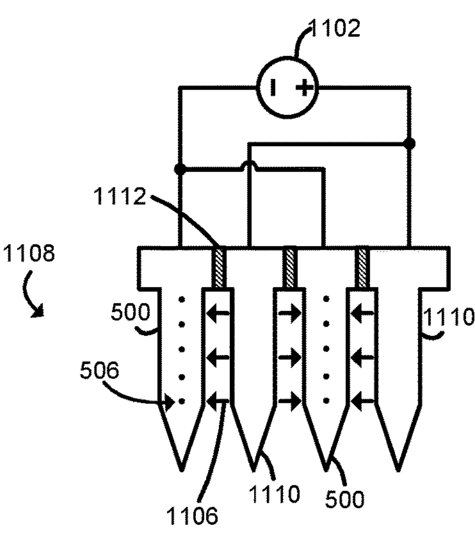

Referring now to FIGS. 11B-11C, it should be appreciated that the needles and electrodes may be configured differently from the configuration shown in FIG. 11A. For example, in one embodiment, a system may include several arrays of needles 1000 and several arrays of electrodes 1100, as shown in FIG. 11B. Additionally or alternatively, in some embodiments, a single array 1108 may include needles 500 interspersed with electrodes 1110, as shown in FIG. 11C. In such an embodiment, each needle 500 may be connected to one side of a voltage source 1102 and each electrode 1110 may be connected to the other side of the voltage source 1102, resulting in the electric fields 1106 as shown. In such embodiments, the needles 500 and electrodes 1110 may be separated by an insulating element 1112.

Figure 12:
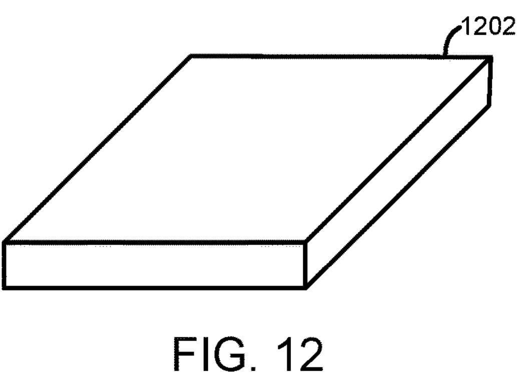
FIG. 12 is one embodiment of a wafer usable to create a needle with microchannels.

Referring now to FIGS. 8-14, various stages of manufacturing of a needle 500 are shown. In FIG. 12, the process begins with a silicon wafer 1202. The silicon wafer may be prepared using standard techniques, such as by cleaning it with solvents and RCA cleaning.

Figure 13:
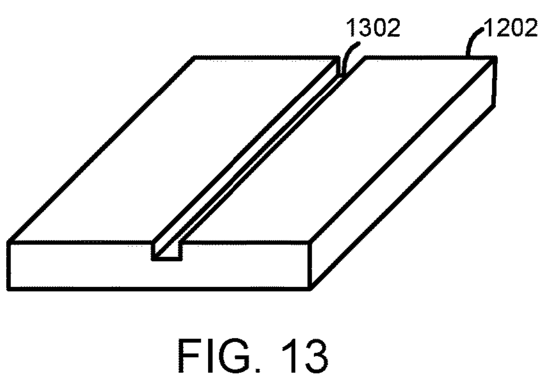
FIG. 13 is one embodiment of a wafer usable to create a needle with microchannels with a channel etched in it.
Figure 14:
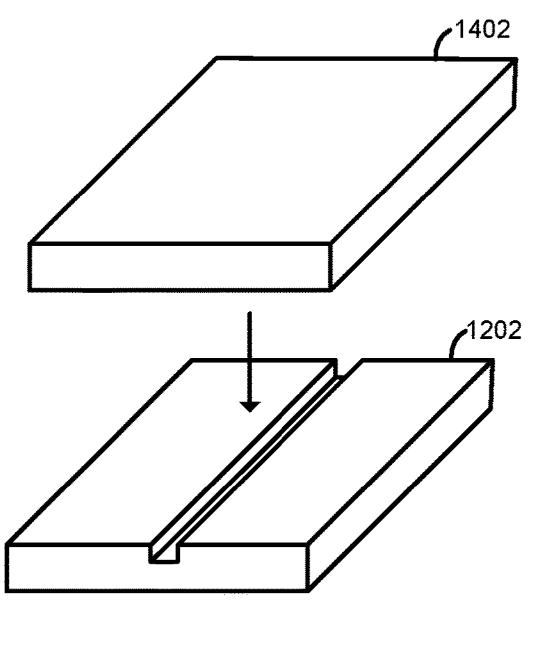
FIG. 14 is one embodiment of a second wafer to be bonded to the wafer of FIG. 13.
Figure 15:
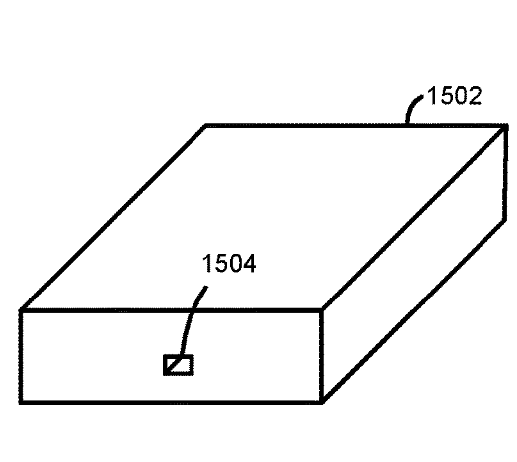
FIG. 15 is one embodiment of a wafer bonded on top of another wafer forming a channel.

The wafer 1202 then has a channel 1302 etched into it, as shown in FIG. 13. The channel 1302 may be etched using standard semiconductor processing techniques. For example, in one embodiment, a photoresist such as AZ1518 is spun onto the wafer. A mask is then used to expose the photoresist by a UV light source over the desired channel location, and the photoresist covering the channel is removed. The channel 1302 is then etched, and the remaining photoresist can be removed and the wafer 1202 can again be cleaned. It should be appreciated that, because the channel 1302 extends along the surface of the wafer 1202, the length of the channel 1302 is not limited by how deep an etching can penetrate below a surface of a wafer. It should be appreciated that, in some embodiments, the channel 1302 may have a different shape than a simple straight channel extending fully along the wafer 1202. For example, the channel 1302 may not extend to one end of the wafer 1202, and/or the channel may have side channels, as shown in FIG. 9. The channel 1302 may have similar dimensions to the primary channel 702 described above.

As shown in FIGS. 10 & 11, a second wafer 1402 is then bonded on top of the wafer 1202, forming a single wafer 1502 with a channel 1504 that is enclosed on all sides except for an opening at one or both ends of the wafer 1502. The wafer 1402 may be bonded to the wafer 1202 using any suitable technique, such as by bonding the wafers 1202, 1402 using a bonding machine and then annealing the wafer 1502 at 400-1,200° C. for 2-8 hours in nitrogen gas to efficiently bond the wafers. The wafer 1402 may be any suitable thickness, such as 10-1,000 micrometers. In some embodiments, the wafer 1402 may be any suitable material, such as plastic, polymer film, or transparent material that is able to be properly bonded to the wafer 1202 or coated on the wafer 1202.

Figure 16:
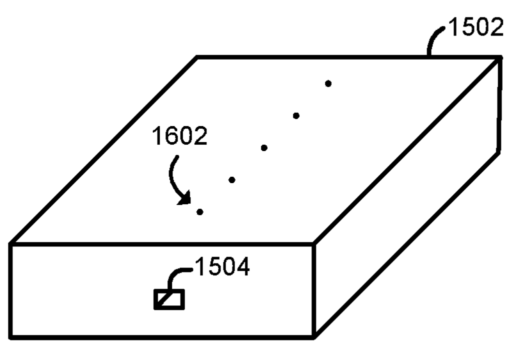
FIG. 16 is one embodiment of the wafer of FIG. 15 with microchannels formed in it.
Figure 17:
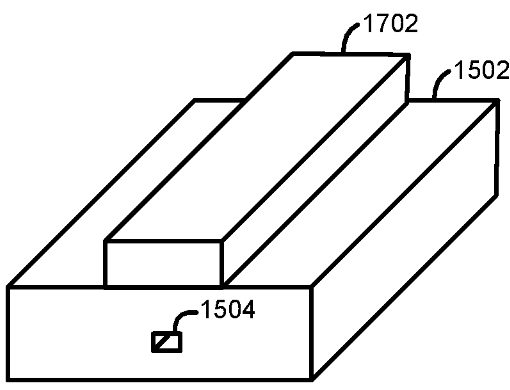
FIG. 17 is one embodiment of the wafer of FIG. 16 with photoresist defining a needle.
Figure 18:
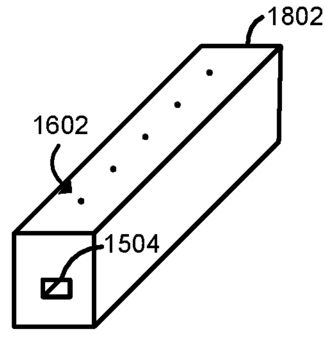
FIG. 18 is one embodiment of a needle with microchannels formed from the wafer of FIG. 17.

Referring now to FIG. 16, one or more microchannels 1602 are formed, extending from the surface of the wafer 1402 to the channel 1504. The microchannels may be formed using photolithography and deep reactive ion etching (DRIE). The microchannels 1602 may have similar dimensions as the microchannels 506 described above.

A photoresist 1702, such as AZ9260, may be applied to the wafer 1502 to define the final shape of a needle. After etching the remaining exposed part of the wafer 1502 and cleaning off the photoresist 1702, a needle 1802 with a channel 1504 and the microchannels 1602 remains. It should be appreciated that, in some embodiments, the needle 1802 that is formed may have a pointed tip, as shown in FIG. 5.

It should be appreciated that the techniques described above may be used to create needles of different shapes and sizes as well as arrays of needles, such as the array of needles 1000. In some embodiments, a single wafer 1202 (combined with a second wafer 1402) may be used to create several separate needles. In some embodiments, the needle 1802 may undergo additional fabrication steps. For example, in the illustrative embodiment, a coating of titanium nitride may be applied to the needle 1802.

It should further be appreciated that the techniques disclosed in regard to FIGS. 8-14 are not the only techniques that can be used to fabricate the needles disclosed herein, such as the needle 500. For example, in some embodiments, the needle 500 or array of needles 1000 may be 3D printed or industrially manufactured.

Figure 19:
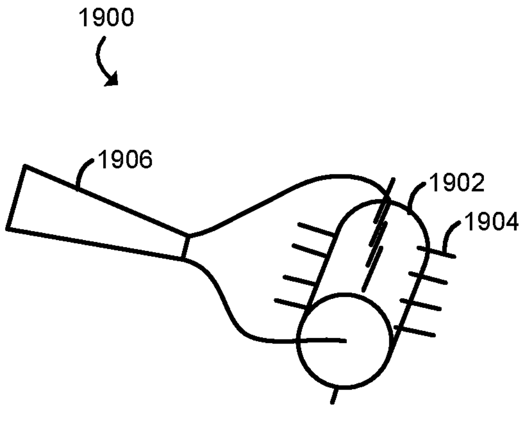
FIG. 19 is one embodiment of a roller system with one or more needles with microchannels.

Referring now to FIG. 19, in one embodiment, a roller system 1900 for administering a drug includes a roller 1902 with one or more needles 1904 attached to it and a handpiece 1906 connected to the roller 1902. Each of the needles 1904 may be similar to the needles 500. In some embodiments, an electrode is disposed next to each needle 1904, such that a voltage can be applied across the needles 1904 and the electrodes to create an electric field, similar to the configuration shown in FIG. 11A. A drug may be administered by moving a plunger of a syringe that is fluidically coupled to the needles 1904, such as through a tube. It should be appreciated that the roller system 1900 may allow for drugs to be delivered through the needles 1904 to a large area simply by rolling the roller system 1900 along an area targeted for treatment.

It should be appreciated that the techniques described here may be suitable for additional embodiments not explicitly described. For example, in some embodiment, a structure with microchannels similar to the microchannels 506 described above may be placed in a patient with use of a catheter or integrated into other surgical tools such as those used for endoscopy or laparoscopy. An electrode may be similarly placed, and the drugs may be delivered through the microchannels 506 and into target cells with use of electroporation, as described above in more detail.

There exists a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

What is claimed is:

1. An apparatus comprising:

a base having a first impermeable surface and an opposing second surface;

a plurality of shafts consisting of silica or plastic and projecting from the second surface of the base to a tip, each of said shafts defining a primary channel interior to each shaft and extending from a proximal end toward a distal end, wherein the proximal end of the primary channel is in fluid communication with said first surface and the distal end of the primary channel terminates within the interior of the shaft defining a primary channel floor, wherein each of said shafts further define one or more microchannels, wherein each of the one or more microchannels extend from the primary channel through the shaft wall to place the primary channel in fluid communication with the exterior surface of the shaft, wherein the major axis of each of the microchannels form an angle relative to the major axis of the primary channel, said primary channel and microchannels formed for receiving a liquid solution comprising a drug; and a first electrode positioned for contact with said liquid solution in the primary channel and a second electrode is positioned adjacent to said shafts, wherein when said first electrode, connected to one side of a voltage source, is placed in contact with the liquid solution introduced into the primary channel and microchannels of each of the shafts, and said second electrode, connected to the other side of said voltage source, are electrically connected, an electric field is created, localized to said microchannels formed in each of the plurality of shafts.

2. The apparatus of claim 1 wherein said second electrode comprises a plurality of electrodes, wherein each of the plurality of electrodes is electrically coupled to each other.

3. The apparatus of claim 1, wherein the diameter of said microchannels is smaller than the diameter of said primary channel, and said primary channel has a diameter selected from the range of about 10 and 1,000 micrometers and the microchannels have a diameter selected from the range of about 1 to 1,000 micrometers.

4. The apparatus of claim 1, wherein the major axis of each microchannel forms a 90° angle with the major axis of the primary channel.

5. A system for inducing electroporation, said system comprising:

a base having a first impermeable surface and an opposing second surface;

a plurality of shafts consisting of silica or plastic and projecting from the second surface of the base to a tip, each of said shafts defining a primary channel interior to each shaft and extending from a proximal end toward a distal end, wherein the proximal end of the primary channel is in fluid communication with said first surface and the distal end of the primary channel is closed, wherein each of said shafts further define a plurality of microchannels extending from the primary channel through the shaft wall to place the primary channel in fluid communication with the exterior surface of the shaft and wherein the major axis of each of the microchannels form an angle relative to the major axis of the primary channel said primary channel and microchannels formed for receiving a liquid solution comprising a drug; and an array of electrodes disposed opposite to said plurality of shafts and configured to match the size and spacing of the shafts of said apparatus, wherein when a first electrode, connected to one side of a voltage source, is positioned to contact said liquid solution introduced into the primary channel and microchannels of each of the shafts, and said array of electrodes is connected to a second side of said voltage source, a voltage is applied to the introduced liquid solution contained within the primary channel and microchannels, and the drug is biased toward said array of electrodes by the generated electric field.

6. The apparatus of claim 5, wherein the electric field is not constant but intermittently applied using pulses of voltage with each pulse lasting between 20 to 100 milliseconds.

* * * * *